United States Patent
Jalisi et al.

(10) Patent No.: US 6,508,832 B1
(45) Date of Patent: Jan. 21, 2003

(54) IMPLANTABLE NICKEL-FREE STAINLESS STEEL STENTS AND METHOD OF MAKING THE SAME

(75) Inventors: Marc M. Jalisi, Temecula, CA (US); David Anderson, Temecula, CA (US); Avijit Mukherjee, Union City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/457,774

(22) Filed: Dec. 9, 1999

(51) Int. Cl.[7] .................................................. A61F 2/06
(52) U.S. Cl. ...................................................... 623/1.15
(58) Field of Search .............................. 623/1.15, 1.34, 623/1.39, 1.42, 1.43, 1.44, 1.46; 606/194, 195; 600/3

(56) References Cited

U.S. PATENT DOCUMENTS

| | | | |
|---|---|---|---|
| 4,743,252 A | 5/1988 | Martin, Jr. et al. | |
| 5,084,065 A | 1/1992 | Weldon et al. | |
| 5,282,823 A | 2/1994 | Schwartz et al. | |
| 5,282,860 A | 2/1994 | Matsuno et al. | |
| 5,342,283 A * | 8/1994 | Good | 600/8 |
| 5,372,779 A * | 12/1994 | Reti | 420/505 |
| 5,443,458 A | 8/1995 | Eury | |
| 5,464,438 A | 11/1995 | Menaker | |
| 5,501,834 A * | 3/1996 | Nakasuji et al. | 420/36 |
| 5,578,564 A * | 11/1996 | Chivers et al. | 514/6 |
| 5,607,442 A | 3/1997 | Fischell et al. | |
| 5,628,787 A | 5/1997 | Mayer | |
| 5,629,077 A | 5/1997 | Turnlund et al. | |
| 5,632,840 A | 5/1997 | Campbell | |
| 5,645,559 A | 7/1997 | Hachtman et al. | |
| 5,667,523 A | 9/1997 | Bynon et al. | |
| 5,723,004 A | 3/1998 | Dereume et al. | |
| 5,725,570 A | 3/1998 | Heath | |
| 5,725,572 A | 3/1998 | Lam et al. | |
| 5,733,326 A * | 3/1998 | Tomonto et al. | 623/1 |
| 5,735,893 A | 4/1998 | Lau et al. | |
| 5,759,192 A | 6/1998 | Saunders | |
| 5,843,166 A | 12/1998 | Lentz et al. | |
| 5,843,172 A | 12/1998 | Yan | |
| 5,848,350 A * | 12/1998 | Bulger | 419/36 |
| 5,858,556 A | 1/1999 | Eckert et al. | |
| 5,891,191 A * | 4/1999 | Stinson | 623/1 |
| 5,895,407 A | 4/1999 | Jayaraman | |
| 5,919,126 A | 7/1999 | Armini | |
| 5,948,018 A | 9/1999 | Dereume et al. | |
| 6,248,190 B1 * | 6/2001 | Stinson | 148/519 |
| 6,258,182 B1 * | 7/2001 | Schetky et al. | 148/402 |
| 6,261,320 B1 * | 7/2001 | Tam et al. | 623/1.15 |
| 6,267,921 B1 * | 7/2001 | Montagnon et al. | 420/57 |
| 6,278,896 B1 * | 8/2001 | Stehlik et al. | 607/35 |

FOREIGN PATENT DOCUMENTS

| | | |
|---|---|---|
| CH | 688 862 | 4/1998 |
| FR | 2 764 307 | 12/1998 |

OTHER PUBLICATIONS

Peter J. Uggowitzer, Ruth Magdowski and Markus O. Speidel, "Nickel Free High Nitrogen Ausenitic Steels", ISIJ International, vol. 36 (1996), No. 7, pp. 901–908.

U.S. patent application Ser. No. 08/837,993, Yan, *Method of Manufacturing A Medicated Porous Metal Prosthesis*, Apr. 15, 1997.

Application of Marc M. Jalisi—Ser. No. 09/270,403—Filed: Mar. 16, 1999—Entitled: Multilayer Stent.

* cited by examiner

Primary Examiner—Corrine McDermott
Assistant Examiner—Alvin Stewart
(74) Attorney, Agent, or Firm—Fulwider Patton Lee & Utecht, LLP

(57) ABSTRACT

The present invention is directed to a stainless steel stent which is substantially nickel-free and possesses improved elongation and mechanical properties, including resistance to corrosion. The stent can be embodied in a substrate with one or more metallic claddings overlaying the substrate. The substrate and claddings can include radiopaque materials and stainless steel.

14 Claims, 2 Drawing Sheets

IMPLANTABLE NICKEL-FREE STAINLESS STEEL STENTS AND METHOD OF MAKING THE SAME

BACKGROUND OF THE INVENTION

The present invention relates to expandable intraluminal vascular grafts, generally referred to as stents. More precisely, the present invention is directed to a stent constructed from stainless steel that is virtually free of any traces of nickel and can have a metallic cladding.

Stents are used to maintain patency of vessels in the body. A variety of delivery systems have been devised that facilitate the placement and deployment of stents. The stent is initially manipulated while in its contracted or unexpanded state, wherein its reduced diameter more readily allows it to be introduced into the body lumen and maneuvered into the target site where a lesion has been dilated. Once at the target site, the stent is expanded into the vessel wall to allow fluid to more freely flow through the stent, thus performing a scaffolding function. Such stents usually are mounted on balloon catheters and are expanded by inflating the balloon on which the stent is mounted. Deflation of the balloon and removal of the catheter leave the stent implanted in the vessel in an expanded state.

Stents are typically formed from biocompatible metals such as stainless steel, nickel-titanium, tantalum, and the like, which provide sufficient hoop strength to perform the scaffolding function. Furthermore, stents have minimal wall thicknesses in order to minimize blood flow blockage. However, stents can sometimes cause complications including thrombosis and neointimal hyperplasia, such as by inducement of smooth muscle cell proliferation at the site of implantation of the stent. Such stents typically also do not provide for delivery of localized therapeutic pharmacological treatment of a blood vessel at the location being treated with the stent, which can be useful for overcoming such problems.

In the evolution of stents, there have been developments in the field of stents coated with a layer of polymers. The polymeric materials are typically capable of absorbing and releasing therapeutic drugs. Examples of such stents are disclosed in U.S. Pat. No. 5,443,358 to Eury; U.S. Pat. No. 5,632,840 to Campbell; U.S. Pat. No. 5,843,172 to Yan; and U.S. Ser. No. 08/837,993, filed Apr. 15, 1997, by Yan.

Aside from coated stents, there have been developments in the field of multilayer grafts. An example of a multilayer graft is disclosed in U.S. Pat. No. 4,743,252 to Martin, Jr. et al. Martin et al. shows a composite graft having a porous wall structure to permit ingrowth, which graft includes a generally non-porous, polymeric membrane in the wall to prevent substantial fluid passage therethrough so as to provide an implantable porous graft that does not require preclotting prior to implantation.

Grafts sometimes have multiple layers for strength reinforcement. For example, U.S. Pat. No. 5,282,860 to Matsuno et al. discloses a stent tube comprising an inner tube and an outer polyethylene tube with a reinforcing braided member fitted between the inner tube and the outer tube. The inner tube is made of a fluorine-based resin.

U.S. Pat. No. 5,084,065 to Weldon et al. discloses a reinforced graft assembly made from a vascular graft component and a reinforcing sleeve component. The reinforcing sleeve component may include one or more layers. The second component of the two component system includes the reinforcing sleeve component. Like the graft component, the reinforcing component includes a porous surface and a porous subsurface. Specifically, the reinforcing sleeve component includes multiple layers formed from synthetic, biologic, or biosynthetic and generally biocompatible materials. These materials are typically biocompatible polyurethane or similar polymers.

Notably, it has been observed that some prior art stents implanted in a body lumen have been prone to corrosion over time. This corrosion can reduce the yield strength of the stent and produce a danger to the patient. Therefore, it would be desirable to produce a stent that has a relatively high resistance to corrosion over the life of the patient.

What has been needed and heretofore unavailable is a substantially nickel-free stent that possesses improved elongation and mechanical properties, including resistance to corrosion. It is also desirable that such a stent have relatively good ductility, yet maintain a high yield strength. The present invention satisfies these and other needs.

SUMMARY OF THE INVENTION

The present invention is directed to an expandable intraluminal vascular graft, generally referred to as a stent. More precisely, the present invention is directed to a stent constructed from stainless steel that is virtually free of any traces of nickel and has a metallic cladding.

In one aspect of the invention, there is provided a stent constructed from stainless steel that is virtually free of any trace of nickel. "Nickel-free" stainless steel has some particular advantages over 316L stainless steel which is a widely used material for manufacturing stents, particularly coronary stents. These advantages include the virtual elimination of nickel which can otherwise cause allergic reactions in some patients when implanted in an artery. Nickel-free stainless steel also can have greater strength and ductility as compared to 316L stainless steel.

In another aspect of the present invention, there is provided a substrate tube having an exterior, wherein the substrate tube is formed from stainless steel that is virtually free of any trace of nickel. A metallic cladding can be mechanically interlocked under pressure over the exterior of the substrate tube. The metallic cladding can include a radiopaque material. A pattern of stent struts can then be formed in the substrate and metallic cladding.

In another aspect, a pattern of stent struts are interconnected to form a structure that contacts a body lumen wall to maintain the patency of the body lumen. The structure includes a substrate made from nickel-titanium, a first metallic cladding made from a stainless steel that is virtually free of any trace of nickel, and a second metallic cladding made from a radiopaque material.

In another aspect of the invention, there is a first cladding mechanically interlocked under pressure over the exterior of the substrate tube. This first cladding can be formed from a radiopaque material. A second cladding then can be mechanically interlocked under pressure over the exterior of the first cladding. The second cladding can be formed from stainless steel that can be virtually free of any trace of nickel. A pattern of stent struts can be formed in the substrate and metallic claddings.

The present invention is also directed to a method of fabricating a stent for implantation within a body lumen including the step of providing a substrate tube having an outside surface and an inside surface, wherein the substrate tube is formed from stainless steel that is virtually free of any trace of nickel. A first cladding tube is disposed over the substrate tube, wherein the first cladding tube includes a radiopaque material selected from the group of radiopaque materials including platinum-10% iridium, platinum, gold, palladium, tantalum, tungsten, and other radiopaque materials. The first cladding tube is joined to the outside surface of the substrate tube to form a laminated tube. Stent struts are then formed in the laminated tube by selectively removing portions of the laminated tube to form a strut pattern.

In another aspect of the invention, a method of fabricating a stent for implantation within a body lumen includes the step of providing a substrate tube having an outside diameter, wherein the substrate tube is formed from stainless steel that is virtually free of any trace of nickel. A first cladding tube is provided having an inside diameter which has an interference fit with the outside diameter of the substrate tube. The first cladding tube may be a radiopaque material selected from a group of radiopaque materials including platinum-10% iridium, platinum, gold, palladium, tantalum, tungsten, and other radiopaque materials. The first cladding tube is disposed over the substrate tube and is joined to the substrate tube to form a laminated tube. A pattern of stent struts are then formed in the laminated tube to create the stent.

The present invention also is directed to a method of fabricating a stent for implantation within a body lumen including the step of providing a substrate sheet having an outside surface and an inside surface, wherein the substrate sheet is formed from stainless steel that is virtually free of any trace of nickel. A first cladding sheet is disposed over the substrate sheet and is joined to the outside surface of the substrate sheet to form a laminated sheet. The first cladding sheet may include a radiopaque material selected from a group of radiopaque materials including platinum-10% iridium, platinum, gold, palladium, tantalum, tungsten, and other radiopaque materials. The laminated sheet is then rolled into a laminated tube. The laminated tube is welded and stent struts are formed in the laminated tube. As a result, the finished stent has a cladding layer laminated onto the nickel-free tubular substrate.

Other features and advantages of the present invention will become more apparent from the following detailed description of the invention, when taken in conjunction with the accompanying exemplary drawings.

DETAILED DESCRIPTION OF THE PREFERRED EMBODIMENTS

Figure 1:
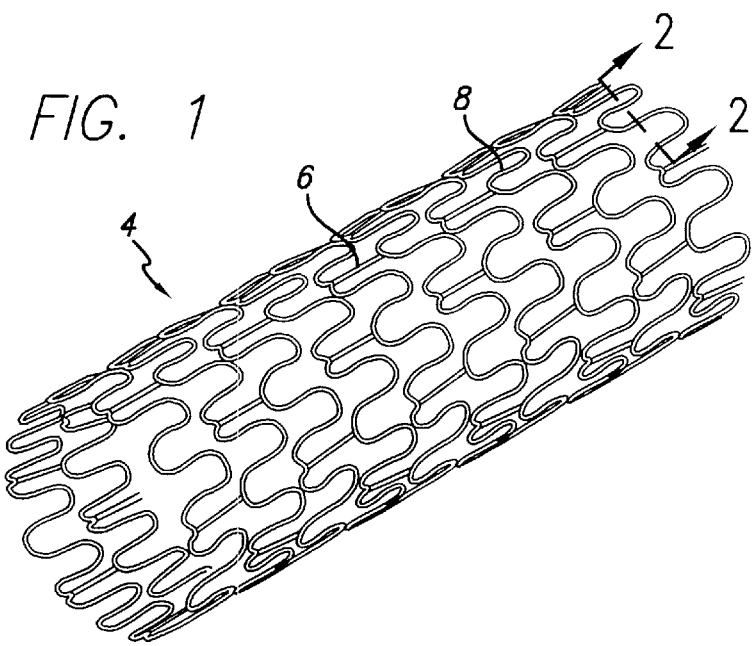
FIG. 1 is a perspective view of a stent of the present invention.

As shown in the exemplary drawings, the present invention is embodied in a metal cladded expandable intraluminal vascular graft, generally referred to as a stent. Like reference numerals indicate like or corresponding elements among the figures.

As explained above, it would be desirable to be able to produce a stent that possesses improved elongation and mechanical properties, including resistance to corrosion. It is also desirable that such a stent have relatively good ductility, yet maintain a high yield strength.

In accordance with the present invention, FIG. 1 illustrates one possible embodiment of a stent 4 for implanting in a body lumen. It is contemplated that many different stent designs can be produced. An intricate pattern of interconnecting members 6 and cylindrical elements (or "rings") 8 can be produced that enable the stent to expand radially when subjected to the appropriate radially directed forces such as are exerted by the inflation of an underlying balloon. These interconnecting members and cylindrical elements are often referred to as "struts." A myriad of strut patterns are known for achieving various design goals such as enhancing strength, maximizing the expansion ratio or coverage area, enhancing longitudinal flexibility or longitudinal stability upon expansion, etc. One pattern may be selected over another in an effort to optimize those parameters that are of particular importance for a particular application.

Figure 2:
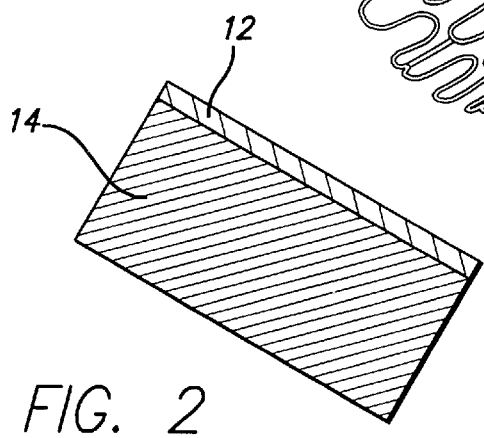
FIG. 2 is an enlarged cross-sectional view taken along lines 2—2 of FIG. 1 illustrating one embodiment of the present invention.
Figure 3:
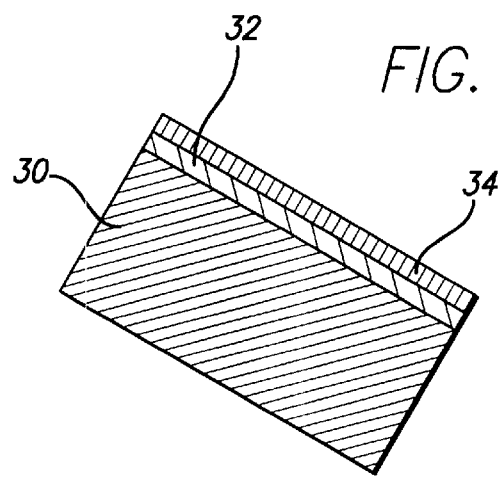
FIG. 3 is an enlarged cross-sectional view similar to that shown in FIG. 2 but of an alternative embodiment of the present invention.

FIG. 2 is a cross-sectional view of one embodiment of stent 4 of the present invention and more specifically, is the cross-section of the strut which forms the cylindrical element 8. The stent includes substrate layer 14 and cladding layer 12. Referring to FIG. 3, an alternative embodiment of the stent includes substrate layer 30, first cladding layer 32, and second cladding layer 34.

Figure 4:
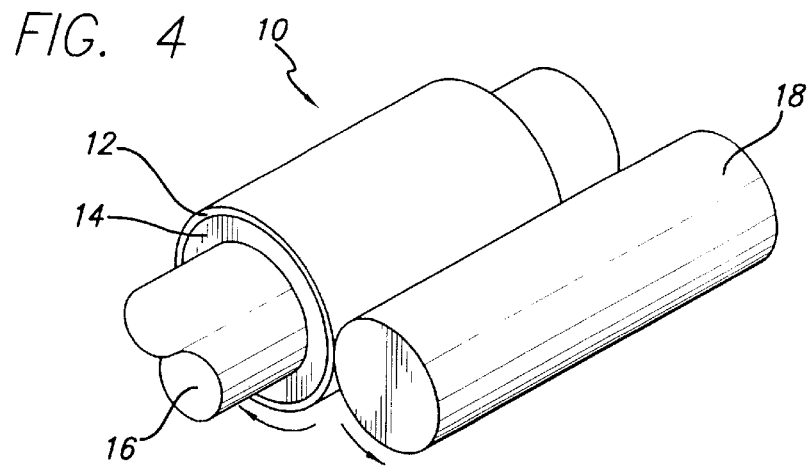
FIG. 4 is a perspective view of one embodiment of a laminated tube mounted on a mandrel and undergoing compression applied by an external roller.

FIG. 4 provides a perspective view of one embodiment of the present invention. As seen in this simplified view, the present invention contemplates creation of a metallic clad stent by joining metal cladding tube 12 to an exterior surface of substrate tube 14 to form a laminated tube 10. Fundamental to this joining process is first defining the initial diameters of metal cladding tube 12, which should already be in a tubular configuration as seen in FIG. 4, and of substrate tube 14. Tubes 12, 14 can be made by conventional fabrication processes, such as drawing, rolling sheet stock and welding the seam, etc. During these preliminary steps, the diameters and wall thicknesses of tubes 12, 14 are selected and set.

Preferably, there should be an interference fit between the outside diameter of substrate tube 14 and the inside diameter of metal cladding tube 12. The interference fit prevents unwanted, relative shifting between substrate tube 14 and the concentrically disposed cladding tube 12.

It is further preferable that the wall thickness of substrate tube 14 be greater than the wall thickness of metal cladding tube 12. The initial wall thicknesses are important, because the present invention processes encompass a deep drawing operation that reduces the diameter and wall thickness of each tube while increasing its length. In order to maintain continuous contact at the interface between the interior of metal cladding tube 12 and the exterior of substrate tube 14, it is preferable that the initial wall thicknesses of the respective parts be as described above.

In concept, the volumes of metal cladding tube 12 and substrate tube 14 are conserved throughout the various cold drawing stages of diameter reduction. Because the outer tube has a larger surface area than the inner tube, its initial wall thickness must be thinner than the initial wall thickness of the inner tube in order to obtain a decrease in diameter proportionate to the inner tube. In this way, the respective diameters of tubes 12, 14 and their wall thicknesses are reduced proportionately and their lengths increased identically thus minimizing the chance of delamination.

In one embodiment, the metal cladding tube 12 is made from a radiopaque material such as platinum-10% iridium, platinum, gold, palladium, tantalum, tungsten, or other radiopaque materials. Accordingly, the present invention can lend improved visibility for the physician. It is also contemplated that the metal cladding tube 12 can also be stainless steel, such as 316L stainless steel. Moreover, the stent can be formed from nickel-free stainless steel only, without any claddings.

Substrate tube 14 is preferably made from stainless steel that is virtually free of any trace of nickel. BioDur® 108 Alloy is one such material that may be used; however, it is contemplated that other suitable materials may be used with the present invention in place of or in addition to BioDur® 108 Alloy.

BioDur® 108 Alloy is available from Carpenter Technology Corporation, 101 West Bern Street, Reading, Pa. 19601, U.S.A. The alloy is a substantially nickel-free austenitic stainless alloy. The alloy contains a high nitrogen content to maintain its austenitic structure. Consequently, the alloy has improved levels of tensile and fatigue strength when compared to such nickel-containing alloys as Type 316L (ASTM F138), 22Cr-13Ni-5Mn Alloy (ASTM F1314), and 734 Alloy (ASTM F1586). Additionally, ductility is not compromised when BioDur® 108 Alloy is used to fabricate a stent instead of 316L stainless steel.

Furthermore, the resistance of BioDur® 108 Alloy to pitting and crevice corrosion is equal to or greater than that of the Type 3 16L Alloy and equivalent to the 22Cr-13Ni-5Mn and 734 Alloys. BioDur® 108 Alloy is non-magnetic and essentially free of ferrite phase. The following table provides a list of elements present in the alloy along with their percentages present by weight. These are typical or average values.

| TYPE ANALYSIS | WEIGHT PERCENTAGE |
|---|---|
| Carbon | 0.08 Max. |
| Manganese | 23 |
| Silicon | 0.75 Max. |
| Phosphorus | 0.03 Max. |
| Sulfur | 0.01 Max. |
| Chromium | 21 |
| Nickel | 0.3 Max. |
| Molybdenum | 0.7 |
| Copper | 0.25 Max. |
| Nitrogen | 0.97 |
| Iron | Balance |

Notably, BioDur® 108 Alloy is useful in applications requiring high levels of strength and corrosion resistance. With respect to some materials, it should be noted that allergic reactions in a small percentage of patients have been observed due to the presence of nickel. The fact that BioDur® 108 Alloy is virtually nickel-free makes it a potential candidate for use in devices that contact the human body in service.

BioDur® 108 Alloy possesses a high resistance to corrosion owed to its high levels of chromium, nitrogen, and molybdenum. BioDur® 108 Alloy exhibits corrosion resistance equivalent to or greater than the nickel-containing alloys, 22Cr-13Ni-5Mn and 734 Alloy. Furthermore, the corrosion resistance of BioDur® 108 Alloy is superior to Type 316L Alloy. BioDur® 108 Alloy possesses a density of 7630 Kg/m$^3$ (0.276 lb/in$^3$).

Notably, BioDur® 108 Alloy is less ferromagnetic than 316L stainless steel. This is important due to the modern medical trend toward noninvasive treatment modality. BioDur® 108 Alloy is compatible with procedures such as magnetic resonance imaging (MRI), CT scanning, and computer tomography.

Annealing of BioDur® 108 Alloy is preferably accomplished in the range of 1040° C. to 1150° C. (1900° F. to 2100° F.). The alloy is typically annealed in the lower part of this range in order to preserve a fine grain size. The alloy is preferably rapidly cooled from the annealing temperature. The reason for this is that slow cooling through the range of 980° C. to 810° C. (1800° F. to 1500° F.) can, under some circumstances, cause precipitation of a chromium nitride phase ($Cr_2N$) that could adversely affect corrosion resistance and toughness.

The choice of materials for metal cladding tube 12 and substrate tube 14 are important and are preferably chosen to assure consistent tube diameter and wall thickness reduction while minimizing the chance of delamination of the concentric tubes. Of course, reversing the material selection for the substrate tube and the cladding tube in specific applications is also contemplated, as are other combinations of materials.

Laminated tube 10 including metal cladding tube 12 over substrate tube 14 is optionally mounted on mandrel 16 and rolled by application of external pinching pressure through roller 18. This is represented in the perspective view of FIG. 4.

Figure 5:
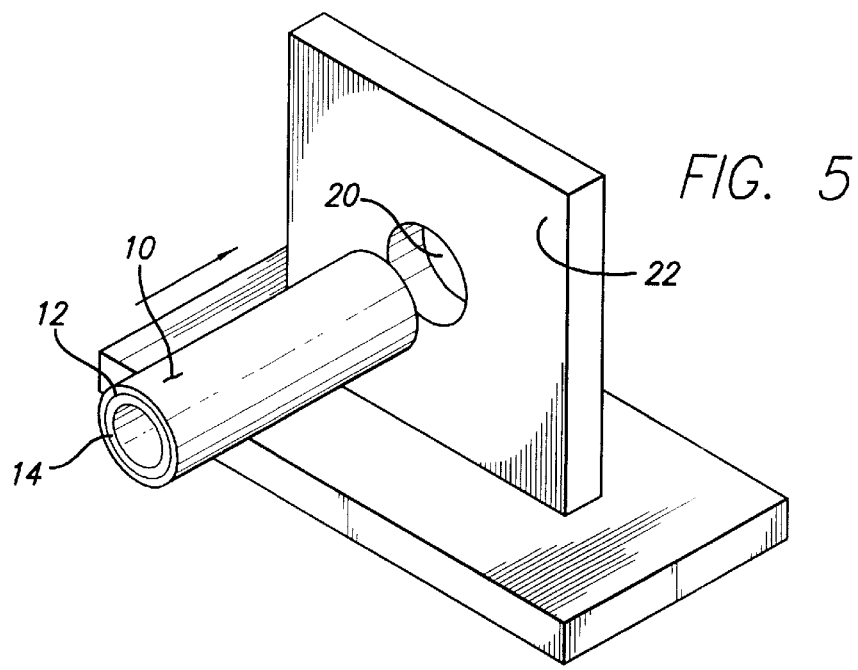
FIG. 5 is a perspective view of a deep drawing operation showing a laminated tube prior to passing through a die.

Along with the rolling operation depicted in FIG. 4, the present invention contemplates a deep drawing operation shown in the perspective view of FIG. 5. Here, laminated tube 10 with metal cladding tube 12 surrounding substrate tube 14 is shown prior to passing through opening 20 of die 22. By passing through a series of dies 22 with sequentially decreasing opening diameters, it is possible to deep draw laminated tube 10 to the final desired diameter. As the name suggests, this cold drawing process is preferably carried out at room temperature, below the recrystallization temperatures of the tube materials.

By repeating the operations shown in FIGS. 4 and 5, it is possible to reduce laminated tube 10 from a starting outside diameter of, for example, ½ inch down to ¹⁄₁₆ inch. The starting wall thickness for the outside tube is approximately ¹⁄₁₆ or ¹⁄₃₂ inch and is reduced down to about 0.003 inch. Of course, the present invention process allows for wall thicknesses ranging from 0.0022 to 0.06 inch. A finished stent might have an outside diameter on the order of about 0.06 inch in the unexpanded condition. The stent can be expanded to an outside diameter of 0.1 inch or more when deployed in a body lumen.

In one embodiment process, the rolling and cold drawing operations are repeated to achieve a maximum of 25 percent in reduction of surface area. Each sequence of operations slowly reduces the diameter of laminated tube 10 while proportionately increasing its length.

Although the present invention rolling and deep drawing processes are conducted at room temperature, the pressures involved cause the temperature between metal cladding tube 12 and substrate tube 14 to elevate sufficiently to create heat fusion between the two materials. Also due to the tremendous pressures involved, a mechanical interlock bond is created between the two adjacent layers. In this manner, metal cladding tube 12 is permanently attached to substrate tube 14 and delamination of the two materials is minimized under normal operating conditions for the stent.

As a result of empirical observations, it is preferred that the material with a smaller coefficient of thermal expansion be used as substrate tube 14. Conversely, the material with a greater coefficient of thermal expansion should be used in metal cladding tube 12. Again, this assures that during the rolling and cold drawing processes the surfaces in common between the two tubes 12, 14 remain in contact and do not delaminate.

In one method, laminated tube 10 undergoes about a twenty-five percent (25%) diameter reduction from the rolling and cold drawing operations. This is accomplished by passing laminated tube 10 through a series of dies 22 with each die reducing the diameter by preferably one percent (1%). With a series of twenty-five dies 22, it is possible to achieve the twenty-five percent (25%) diameter reduction.

Laminated tube 10 then undergoes another twenty-five percent (25%) diameter reduction by cold drawing and rolling. This cycle is repeated until the desired diameter of laminated tube 10 is reached. Throughout the present invention process, laminated tube 10 may optionally undergo anneal cycles in order to impart desired material properties such as ductility, strength, etc. It should be noted that processes for hardening BioDur® 108 Alloy by heat treatment are not currently known but it may be hardened by cold working.

Through the present invention process, it has been observed that the finished composite stent has a straightness of 0.02 inch per inch for a six to twelve inch length tube. In other words, there is virtually no curvature or bend in the finished stent. When the final diameter is reached, the tubes are cut to specific lengths. Laminated tube 10, which has now been cladded with metal tube 12, is further processed to form stent struts. Stent struts may be formed by a laser cutting process. Such a process is shown and disclosed in, for example, U.S. Pat. No. 5,759,192 to Saunders, entitled "Method and Apparatus for Direct Laser Cutting of Metal Stents," whose entire contents are hereby incorporated by reference. Another method for forming such stent struts is by chemical etching. Such a process is disclosed in, for example, U.S. Pat. No. 5,735,893 to Lau et al., entitled "Expandable Stents and Method for Making Same," whose contents are incorporated herein by reference. The laminated tube 10 will end up looking like the stent of FIG. 1 or possess another desired design.

Figure 6:
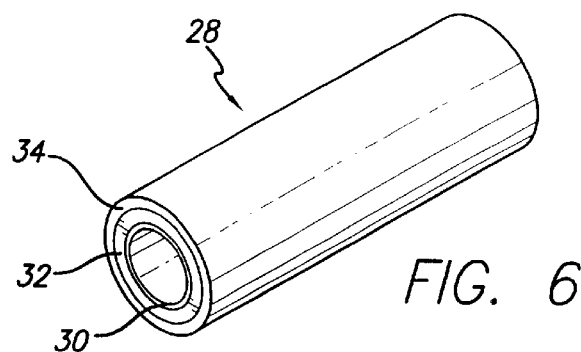
FIG. 6 is a perspective view of another embodiment of a laminated tube.

FIG. 6 provides a perspective view of an alternative embodiment showing laminated tube 28 including substrate tube 30 that is laminated with first metallic cladding tube 32. The first cladding tube can include a radiopaque material selected from the group of radiopaque materials including platinum-10% iridium, platinum, gold, palladium, tantalum, tungsten, and other radiopaque materials. The substrate tube 30 can be formed from stainless steel that is virtually free of any trace of nickel, such as BioDur® 108 Alloy. Second metallic cladding tube 34 is laminated to the outer surface of first metallic cladding tube 32. The second cladding tube can include a metal selected from the group of metals including stainless steel. The stainless steel can be chosen to be virtually nickel-free.

It is also contemplated that substrate 30 can be made from nickel-titanium, first metallic cladding 32 can be made from a stainless steel that is virtually free of any trace of nickel, and second metallic cladding 34 can be made from a radiopaque material.

The multiple layers of cladding of composite stent 28 are created as previously described in connection with FIGS. 4 and 5, except that second metallic cladding tube 34 is added to the outside surface of first metallic cladding tube 32. The three tubes 30, 32, 34 then undergo the rolling an cold drawing operations as described previously. When the final diameter is reached, composite stent 28 is cut to the desired length and processed to form a stent resembling the stent of FIG. 1 or possess another desired design.

Figure 7:
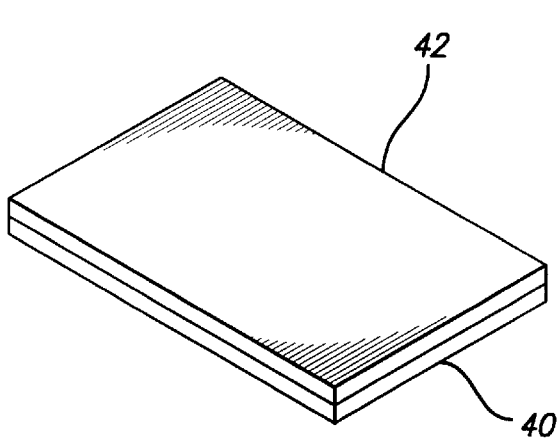
FIG. 7 is a perspective view of a step in the process of manufacturing a stent out of sheets of metal.

Referring to FIG. 7, it is also contemplated that stent 4 can be manufactured in a similar manner using sheets instead of tubes. A substrate sheet 40 is provided having an outside surface and an inside surface, wherein the substrate sheet is formed from stainless steel that is virtually free of any trace of nickel, such as BioDur® 108 Alloy. A first cladding sheet 42 is disposed overlaying the substrate sheet, wherein the first cladding sheet includes a radiopaque material selected from the group of radiopaque materials including platinum-10% iridium, platinum, gold, palladium, tantalum, tungsten, and other radiopaque materials. The first cladding sheet is joined to the outside surface of the substrate sheet to form a laminated sheet. The laminated sheet is rolled into a laminated tube. The laminated tube is welded and stent struts are formed in the laminated tube by chemical etching or laser cutting.

It is contemplated that second cladding sheet can be provided including a metal selected from the group of metals including stainless steel, such as Type 316L. The second cladding sheet is disposed overlaying first cladding sheet 42 and then joined to the first cladding sheet. Alternatively, a second cladding sheet can be joined to the laminated sheet. Preferably, the first cladding sheet has a wall thickness that is less than that of the substrate sheet. As described above, the steps of deep drawing and cold working can be used in the manufacturing process.

Consequently, a stent may be produced exhibiting improved elongation and mechanical properties, including resistance to corrosion. The stent further has relatively good ductility, yet maintains a high yield strength.

While the invention has been illustrated and described herein in terms of its use a stainless steel stent formed from stainless steel that is virtually free of any trace of nickel, such as BioDur® 108 Alloy, it will be apparent to those skilled in the art that the invention can be used in other instances. For example, the dimensions and materials referenced herein are by way of example only and not intended to be limiting. Thus, certain stent dimensions may vary to suit a particular application. Additionally, any of a variety of stent designs and applications can benefit from the present invention. Furthermore, stainless steel that is virtually free of any trace of nickel, such as BioDur® 108 Alloy, cay be used in other medical components that contact the human body in service. Other modifications and improvements may be made without departing from the scope of the invention.

What is claimed is:

1. A stent for implantation in a body lumen of a patient, comprising:
   a pattern of non-overlapping struts interconnected to form a structure that contacts a body lumen wall to maintain the patency of the body lumen, wherein the struts are made from stainless steel that is virtually free of any trace of nickel and wherein the amount of nickel in the structure is less than or equal to 0.3 percent by weight.

2. The stent of claim 1, wherein the structure has a substrate and a first metallic cladding.

3. The stent of claim 2, wherein the substrate is made from stainless steel that is virtually free of any trace of nickel and the first metallic cladding is selected from the group of radiopaque materials including platinum-10% iridium, platinum, gold, palladium, tantalum, tungsten, and other radiopaque materials.

4. The stent of claim 2, wherein the structure has a second metallic cladding.

5. The stent of claim 4, wherein the second metallic cladding includes a metal selected from the group of metals including stainless steel.

6. A stent for implantation in a body lumen of a patient, comprising:
 a pattern of struts interconnected to form a structure that contacts a body lumen wall to maintain the patency of the body lumen, wherein the structure includes a substrate made from nickel-titanium alloy, a first metallic cladding made from a stainless steel that is virtually free of any trace of nickel wherein the amount of nickel in the structure is less than or equal to 0.3 percent by weight, and a second metallic cladding made from a radiopaque material.

7. The stent of claim 6, wherein the structure is constructed from BioDur® 108 Alloy.

8. The stent of claim 6, wherein the second metallic cladding is selected from the group of radiopaque materials including platinum-10% iridium, platinum, gold, palladium, tantalum, tungsten, and other radiopaque materials.

9. A stent for implantation within a body lumen, comprising:
 a substrate tube having an exterior surface, wherein the substrate tube is formed from stainless steel that is virtually free of any trace of nickel wherein the amount of nickel in the structure is less than or equal to 0.3 percent by weight;
 a metallic cladding mechanically interlocked under pressure over the exterior surface of the substrate tube; and
 a pattern of non-overlapping stent struts formed in the substrate and metallic cladding.

10. The stent of claim 9, wherein the cladding includes a radiopaque material selected from the group of radiopaque materials including platinum-10% iridium, platinum, gold, palladium, tantalum, tungsten, and other radiopaque materials.

11. The stent of claim 9, wherein a wall thickness of the cladding is less than a wall thickness of the substrate tube.

12. The stent of claim 9, wherein the stent includes a second layer of metallic cladding mechanically interlocked under pressure to an exterior of the cladding over the substrate tube.

13. The stent of claim 9, wherein the metallic cladding is formed from a stainless steel selected from the group of stainless steels including Type 316L stainless steel.

14. A stent for implantation within a body lumen, comprising:
 a substrate tube having an exterior surface, wherein the substrate tube is formed from stainless steel that is virtually free of any trace of nickel wherein the amount of nickel in the structure is less than or equal to 0.3 percent by weight;
 a first cladding mechanically interlocked under pressure over the exterior surface of the substrate tube, wherein the first cladding is formed from a radiopaque material;
 a second cladding mechanically interlocked under pressure over the exterior of the first cladding, wherein the second cladding is formed from stainless steel that is virtually free of any trace of nickel; and
 a pattern of non-overlapping stent struts formed in the substrate and metallic cladding.

* * * * *